United States Patent
Tjioe (12)

(10) Patent No.: US 6,548,669 B2
(45) Date of Patent: Apr. 15, 2003

(54) METHOD FOR PREPARING MELAMINE

(75) Inventor: Tjay T. Tjioe, Sittard (NL)

(73) Assignee: DSM N.V., Heerlen (NL)

(*) Notice: Subject to any disclaimer, the term of this patent is extended or adjusted under 35 U.S.C. 154(b) by 0 days.

(21) Appl. No.: 09/828,999

(22) Filed: Apr. 10, 2001

(65) Prior Publication Data

US 2002/0004597 A1 Jan. 10, 2002

Related U.S. Application Data

(63) Continuation of application No. PCT/NL99/00362, filed on Jun. 18, 1999.

(30) Foreign Application Priority Data

Oct. 14, 1998 (NL) .............................................. 1010316

(51) Int. Cl.$^7$ ..................... C07D 251/60; C07D 251/62
(52) U.S. Cl. ....................................... 544/201; 544/203
(58) Field of Search ................................. 544/201, 203

(56) References Cited

U.S. PATENT DOCUMENTS

| | | | |
|---|---|---|---|
| 3,116,294 A | 12/1963 | Marullo | .................... 260/249.7 |
| 6,252,074 B1 * | 6/2001 | Noe | ........................... 544/201 |
| 6,254,840 B1 * | 7/2001 | Mennen et al. | ............. 422/195 |

FOREIGN PATENT DOCUMENTS

WO    WO 9900374    1/1999

OTHER PUBLICATIONS

Kirk–Othmer, "Powder Coatings to Recycling"—Encyclopedia of Chemical Technology, 3rd edition, vol. 19, p. 886, 1982.

* cited by examiner

Primary Examiner—John M. Ford
Assistant Examiner—Venkataraman Balasubramanian
(74) Attorney, Agent, or Firm—Pillsbury Winthrop LLP

(57) ABSTRACT

A method for the production of melamine from urea via a high-pressure non-catalytic process in which molten urea is reacted to produce melamine, carbon dioxide, and ammonia, the by-product gases are separated from the melamine melt, and the melamine melt is treated with ammonia in a liquid-filled column to remove dissolved carbon dioxide, the treated melamine melt being solidified to produce high-purity melamine. In the liquid-filled column, or bubble column, the melamine melt is treated with between 0.02 and 3 tons of ammonia per ton of melamine, the bubble column being operated at a pressure of between 1 and 40 MPa and at a temperature between the melting point of melamine at prevailing pressure and 450° C., with the residence time of the melamine melt in the bubble column being between 1 minute and 10 hours.

19 Claims, No Drawings

METHOD FOR PREPARING MELAMINE

This is a continuation of International Application No. PCT/NL99/00362 filed Jun. 18, 1999 which designates the U.S., and that International Application was published under PCT Article 21(2) in English.

The invention relates to a method for preparing melamine by causing liquid urea to react and form a melamine melt, separating the melamine melt from gaseous products formed in the reaction, and treating the melamine melt with ammonia in order to remove a majority of the dissolved carbon dioxide.

Such a method is described in, inter alia, U.S. Pat. No. 3,116,294 which discloses preparing melamine by converting urea into melamine, carbon dioxide, and ammonia, with the bulk of the melamine forming a liquid phase, and the bulk of the carbon dioxide and ammonia forming a gas phase. The gas phase is then separated from the liquid phase, with the melamine melt then being treated with ammonia to remove dissolved carbon dioxide. Although, according to U.S. Pat. No. 3,116,294, the disclosed method is suitable for producing high purity of melamine, the disclosure does not provide a specific method of implementing the disclosed method on an industrial scale.

A common method for purifying a liquid stream is to use a stripping process in which the impurities are removed with the aid of a gas passed through the liquid. Stripping processes are often carried out in gas-filled packed columns or gas-filled tray columns.

Packed columns are columns filled with bodies (packings) that promote the contact between the different phases present in the column. These bodies may be obtained in a wide variety of shapes, such as spheres, rings, and saddles, sizes, and compositions. The bodies may be deployed in the packed column as random packings or may comprise specific units that are stacked on top of one another (structured packings). In a gas-filled packed column, the gas phase is the continuous phase, with the liquid phase typically flowing down through and along the packing as a film, thereby providing a large contact area between the liquid and gas phases.

A tray column, however, typically includes a number of trays or plates that divide the column into a number of distinct compartments. Commonly the trays will be positioned parallel to each other and spaced evenly along an axis of the column. In operation, a tray column will typically maintain a thin layer of liquid on each tray with a large gas-filled space between the trays in order to suppress entrainment and flooding. The term entrainment refers to a condition in which liquid droplets are dragged or blown from one compartment to the next compartment by the gas flow. In countercurrent operation, the entrained liquid droplets will be forced in a direction opposite from the bulk liquid flow. The term flooding refers to a condition in which the liquid phase fills a compartment, eliminates the desired gas space between compartments, and begins to flow into an adjacent compartment. Uncorrected, a flooding condition will fill the column with the liquid phase flowing in a direction opposite the desired flow. It has been found that using gas-filled packed columns and tray columns for stripping a melamine melt, particularly operating at high pressures, achieves unsatisfactory results either in terms of purity or energy and gas consumption.

The applicant has now found that it is possible, without increasing the size of the stripping unit or increasing the volume of ammonia employed, to achieve much better stripping of carbon dioxide from a melamine melt. This improvement is obtained by using a liquid-filled stripping column, also referred to as a bubble column, to remove dissolved carbon dioxide from the melamine melt. According to the present invention, the bubble column uses between 0.02 and 3 tons of ammonia per ton of melamine melt while operating at a pressure of between 1 and 40 MPa, at a temperature between the melting point of melamine at the operating pressure and 450° C., and providing a residence time of between 1 minute and 10 hours for the melamine melt. Preferably, a bubble column according to the present invention will use between 0.1 and 1 ton of ammonia per ton of melamine while operating at a pressure of between 4 and 25 MPa and provide a residence time for the melamine melt of between 10 minutes and 3 hours within the stripper.

This method of operating a bubble column for stripping a melamine melt differs significantly from methods using a gas-filled packed column in that the ammonia gas, rather than being the continuous phase, exists as bubbles in melamine melt that forms a continuous liquid phase. The bubble column can be operated with crosscurrent, cocurrent, or countercurrent flows of the respective gas and liquid phases. The ammonia gas throughput and the column diameter are preferably chosen such that the superficial gas velocity based on the total column cross-section is between 0.001 and 0.2 m/sec, and more preferably between 0.003 and 0.1 m/sec. The term superficial gas velocity refers to the volume flow of the gas (in $m^3$/sec) at the operating pressure divided by the column diameter (in $m^2$).

A bubble column according to the present invention is preferably provided with a packing. If present, the packing can either be a random or a structured packing, so long as the packing provides sufficient open space for the flow of the desired amount of ammonia gas. Preferably, the gas flow will be distributed evenly across the column cross-section. If a packing is used, it is preferable to select a packing having a specific surface area of between 10 and 3000 $m^2/m^3$, and more preferably, between 25 and 600 $m^2/m^3$.

More preferably, the bubble column, rather than employing a packing, is divided by a number of plates into a plurality of compartments in which the liquid is treated with ammonia gas, with the gas being incorporated into the melamine melt in a crosscurrent, countercurrent, or cocurrent flow pattern. A combination of different flow patterns, a combination of a packed column and a tray column, or a combination of packed and tray regions within a single column are obviously also possible.

If the bubble column is divided into compartments by a series of trays or plates, the number of compartments is preferably less than 500, and more preferably 100 or less. The plates used to separate the compartments may be solid or perforated. If the plates are perforated, the perforations may be sized and configured to allow or promote the flow of the melamine melt, the ammonia gas, or both. The term plate should not be construed as limited to a generally planar structure but rather should be understood to encompass a variety of structural configurations that may be used to divide a column into a plurality of compartments.

In a first embodiment, the compartments are situated next to one another and are separated by one or more plates, either solid or perforated, to define a plurality of separate pipes that at least partially filled with the melamine melt. In another embodiment, the compartments are situated underneath one another in a stacked configuration and are separated by one or more plates, either solid or perforated, positioned generally horizontally across the bubble column.

If a plate is perforated in a manner designed to permit gas flow through at least some of the perforations, a certain gas velocity will be achieved through those perforations. According to the present invention, the number and size of such perforations should be chosen to produce a gas velocity of between 0.01 and 100 m/sec, preferably between 0.2 m/s and 20 m/s, through the perforations. In particular, it has been found that perforations between 0.1 and 200 mm, and more preferably, between 0.5 mm and 100 mm, can be used to achieve such gas velocities. For a given plate, the total area of perforations designed for gas flow is preferably between 0.02% and 30% of the bubble column cross-sectional area. Alternatively, if the plates are not perforated, sufficient space must be provided between the wall of the column and the plates for the required liquid and the gas flows. Although gas and liquid can flow through the same perforations, it is preferable to provide separate perforations for the gas and liquid flows. Also, it is preferable to distribute the perforations designed for gas flow evenly over the column cross-section.

Consistent with the present invention, it is also possible to employ a combination of a bubble column with packings and bubble column with compartments or to provide both packed regions and compartments within a single bubble column. Further, regardless of the particular configuration of bubble column selected, the disclosed stripping process may be carried out as either a batch or a continuous process.

An essential difference between the bubble column of the present invention and the gas-filled columns customarily used for stripping a melamine melt is the increased liquid hold-up during operation. This liquid hold-up is defined by the following equation:

$$\frac{\text{(dynamic liquid volume in stripping zone)}}{\text{(column volume in stripping zone)}}$$

As used here, the term dynamic liquid volume means the total liquid volume minus the static liquid volume. (For experimental measurement see: H. Z. Kister, *Distillation Design*, McGraw-Hill (1992), chapter 8.2.14). The term "stripping zone" refers to that section of the stripping column between the location where the stripping gas first comes into contact with the liquid and the location where the majority of stripping gas is removed from contact with the liquid.

The design of conventional stripping columns (gas-filled packed or tray columns) is intended to achieve low liquid hold-up, generally less than 20%, given good design, and often less than 10%. In contrast, a bubble column according to the present invention is designed to provide a liquid hold-up of at least 35%, preferably greater than 50%, and most preferably greater than 70%.

It is also advantageous for the present method to be implemented in such a way that the melamine melt being stripped in the bubble column is cooled simultaneously to a temperature between the inlet temperature and the crystallization temperature of the melamine melt. This cooling is preferably achieved by introducing ammonia gas having a temperature of between 150° C. and 350° C. into the stripper.

The advantage of the present invention is that the final melamine is obtained with a considerably lower level of oxygen-containing compounds than achieved by gas-filled column stripping. Examples of oxygen-containing compounds are ammeline, ammelide, urea, cyanuric acid and ureidomelamine. In particular, using the present method, a melamine end product can be obtained with a level of oxygen-containing compounds consistently below 0.7 wt %.

Preferably, the process conditions should also be selected to suppress the formation of deammoniation by-products, and in particular maintain the melam content below 1.5 wt %, to achieve an end product melamine purity of more than 98.5 wt %.

This result can be achieved by maintaining a sufficiently high ammonia pressure over the melamine melt, the necessary pressure being dependent on the temperature of the melamine melt, and by employing the present invention to remove carbon dioxide and oxygen-containing compounds in a bubble column. Although, for a given temperature, using higher ammonia pressure will reduce the melam content of the melamine melt, higher ammonia pressure will also increase the amount of ammonia necessary to maintain an equal stripping efficiency.

The present invention provides for the design and operation of a bubble column in which dissolved carbon dioxide may be removed from a melamine melt with the aid of ammonia.

The invention also provides for a bubble column in which the melamine melt is simultaneously stripped and cooled to a temperature between the inlet temperature and the crystallization temperature of the melamine melt using ammonia gas having a temperature of between 150° C. and 350° C.

The preparation of melamine according to the present invention preferably starts with molten urea as the raw material. In a reactor at suitable temperatures and pressures, the molten urea will react according to the following equation to produce melamine, $NH_3$, and $CO_2$:

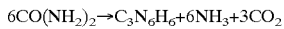

$$6CO(NH_2)_2 \rightarrow C_3N_6H_6 + 6NH_3 + 3CO_2$$

This reaction can be carried out at high pressure, preferably between 4 and 25 MPa, without employing a catalyst, and at high temperatures, preferably between 350 and 425° C. The by-product gases, $NH_3$ and $CO_2$, are then generally separated from the melamine melt and preferably recycled to an adjoining urea production facility.

In one embodiment of the invention, melamine is prepared from urea in an apparatus comprising a scrubber unit, a melamine reactor, a gas/liquid separator, a bubble column, and a product cooling unit. Preferably, the gas/liquid separator is combined with the bubble column into a single unit. The production of melamine from urea using this apparatus begins with the urea melt being fed to the scrubber unit at a pressure of from 1 to 40 MPa, preferably from 4 to 25 MPa, and at a temperature above the melting point of urea. The scrubber unit may be provided with a cooling jacket or internal cooling bodies in order to provide additional cooling.

In the scrubber unit the liquid urea contacts the reaction gases from the gas/liquid separator. The reaction gases mainly consist of $CO_2$ and $NH_3$ and also comprise a minor amount of melamine vapor. The molten urea scrubs the melamine vapor from the reaction gases and cools the gases from the reactor temperature, i.e. from 350 to 425° C., to from 170 to 240° C., while heating the urea melt to from 170 to 240° C. The scrubbed reaction gases are removed from the top of the scrubber unit and preferably recycled to an adjoining urea factory to be used as raw materials for urea production.

The preheated urea melt, together with melamine scrubbed from the reaction gases, is fed into the reactor, the reactor operating at a pressure of from 1 to 40 MPa, preferably from 4 to 25 MPa, and at a temperature between the melting point of melamine and 450° C. The transfer of the urea melt from the scrubber to the reactor can be achieved with high-pressure pump, or alternatively, at least partially by gravity, if the scrubber unit is positioned above the reactor.

In the reactor, the molten urea is heated to a temperature of from 325 to 450° C., preferably from approximately 350 to 425° C., at a pressure between 1 and 40 MPa, to convert the urea into melamine, $CO_2$, and $NH_3$. Additional ammonia can be metered into the reactor, as either a liquid or hot gas, to suppress the formation of condensation (deammoniation) products of melamine such as melam, melem, and melon, and/or to promote mixing in the reactor. The amount of ammonia supplied to the reactor is generally proportional to the amount of urea entering the reactor and may be up to 10 moles of ammonia, preferably up to 5 moles of ammonia, and most preferably, between 0.1 to 2 moles of ammonia, per mole of urea.

The $CO_2$ and $NH_3$ produced in the reaction, as well as the majority of the additional ammonia added to the reactor, are removed from the melamine melt in either a separate gas/liquid separator or, more preferably, in the combination gas/liquid separator and bubble column. Additional ammonia is also metered into the bubble column at a rate of 0.02–3 tons of ammonia per ton of melamine to promote the removal of dissolved carbon dioxide. It is believed that the advantage of the present invention is the suppression of oxygen-containing by-products by rapidly removing the majority of the dissolved carbon dioxide from the melamine melt by treatment with ammonia in the bubble column.

The gas mixture removed from the gas/liquid separator is fed in the scrubber unit as described above to remove melamine vapor and preheat the urea melt.

If the melamine melt from the bubble column is at a temperature above the melting point of melamine, the melamine melt may be cooled to a temperature to a lower temperature that is still above the melting point of melamine. The liquid melamine leaving the reactor preferably has a temperature above 380° C., may be cooled at least 5° C., more preferably cooled at least 15° C., and, most preferably, cooled to a temperature which is 5–20° C. above the solidification point of melamine. This cooling may take place in the gas/liquid separator, in the bubble column, or in a separate cooling unit, employed separately or in combination. The desired cooling can be achieved by injecting a cooling medium, for example ammonia gas or liquid ammonia, or in a heat exchanger, either provided separately or incorporated into another unit such as the bubble column.

The melamine melt, preferably together with some ammonia gas, is then transferred to a spraying means, such as a nozzle or a valve, and sprayed into the product cooling unit. In the product cooling unit, the melamine melt may be cooled further by mixing with a cooling medium such as liquid ammonia or cool ammonia gas. An ammonia atmosphere is preferably maintained within the product cooling unit, the ammonia pressure being maintained at a pressure of between 0.1 and 25 MPa. In the product cooling unit the melamine melt is solidified and cooled to produce a melamine powder with a temperature below the solidification point of melamine.

The invention is explained in more detail with reference to the following examples.

EXAMPLE I

A melamine melt having a level of 2.3% of oxygen-containing compounds is stripped with ammonia. The stripper is divided into six compartments, one above the other, with perforated (sieve) plates in between, operated as a liquid-filled bubble column. Each sieveplate has 6 holes for the gas flow with a diameter of 1 mm. The sieveplate has a skirt at the edge of the plate directed downwards to prevent the-gas flowing between the wall and the sieveplate. The melamine melt flows downwards from one compartment to the other through a downcomer. The pressure in the stripper is 18.2 MPa and the temperature is 366° C. Ammonia gas is fed into the bottom of the stripper at a rate of 1.3 kg/hour and the melamine melt is fed into the top of the stripper at a rate of 1.6 kg/hour to produce a countercurrent flow. The stripper has an internal diameter of 4 cm and a liquid column height of 2 m. The liquid hold-up in the bubble column is more than 97%. After stripping, the end product contains only 0.21 wt % of oxygen-containing compounds and has a melamine content of 99.2 wt %.

COMPARATIVE EXAMPLE A

A melamine melt having a level of 2.3% of oxygen-containing compounds is stripped with ammonia. The stripper of Example 1 is again used, but is operated as a traditional gas-filled stripping column with only a thin layer of the liquid phase on the sieve plates. Ammonia gas is fed into the bottom of the stripper at a rate of 1.3 kg/hour and the melamine melt is fed into the top of the stripper at a rate of 1.6 kg/hour to produce a countercurrent flow. The pressure in the stripper is 18.2 MPa and the temperature is 366° C. The liquid hold-up in the gas-filled column is less than 10%. After stripping, the end product contains 1.1 wt % of oxygen-containing components and has a melamine content of 98.3 wt %.

EXAMPLE II

A melamine melt having a level of 2.1% of oxygen-containing compounds is stripped with ammonia. The stripper is filled with packings having a specific surface area of 250 $m^2/m^3$ and is operated as a liquid-filled bubble column. The pressure in the stripper is 18.1 MPa and the temperature is 369° C. Ammonia gas is fed into the bottom of the stripper at a rate of 1.3 kg/hour and the melamine melt is fed into the top of the stripper at a rate of 1.6 kg/hour to produce a countercurrent flow. The stripper has an internal diameter of 4 cm and a liquid column height of 2 m. The liquid hold-up in the bubble column is more than 95%. After stripping, the end product contains only 0.18 wt % of oxygen-containing compounds and has a melamine content of 99.0%.

COMPARATIVE EXAMPLE B

A melamine melt having a level of 2.1% of oxygen-containing compounds is stripped with ammonia. The stripper of Example 2 is again used, but is operated as a traditional gas-filled stripping column with only a thin layer of the liquid phase on the packing. Ammonia gas is fed into the bottom of the stripper at a rate of 1.3 kg/hour and the melamine melt is fed into the top of the stripper at a rate of 1.6 kg/hour to produce a countercurrent flow. The pressure in the stripper is 18.1 MPa and the temperature is 369° C. The liquid hold-up in the gas-filled column is less than 10%. After stripping, the end product contains 1.0 wt % of oxygen-containing components and has a melamine content of 98.2 wt %.

What is claimed is:

1. Method for preparing melamine comprising reacting urea in the melt, separating the resulting melamine melt from gaseous products formed in the reaction, treating said melamine melt in a column with ammonia in order to remove the carbon dioxide dissolved in the melamine melt, the amount of ammonia used in the melt being between 0.02 and 3 tons per ton of melamine, the column being operated at a pressure of between 1 and 40 MPa and the temperature in the column being between the melting point of melamine at prevailing pressure and 450° C., and the residence time of the melamine melt in the column being between 1 minute and 10 hours, and wherein said column is a bubble column filled with a packing or divided into a plurality of compartments or provided with both packed regions and a plurality of compartments, and wherein the bubble column has a liquid hold-up of a least 35%, said liquid hold-up being defined as:

$$\text{liquid hold-up} = \frac{\text{(dynamic liquid volume in stripping zone)}}{\text{(column volume in stripping zone)}}.$$

2. Method according to claim 1, wherein the bubble column is provided with packing.

3. Method according to claim 2, wherein the packing has a specific surface area of between 10 and 3000 $m^2/m^3$.

4. Method according claim 1, wherein the treatment with ammonia takes place in a bubble column having from 2 to 100 compartments.

5. Method according to claim 4, wherein the compartments are situated next to one another and are separated by 1 or more partitions.

6. Method according to claim 4, wherein the compartments comprise separate pipes which are entirely or partially filled with melamine melt.

7. Method according to claim 4, wherein the compartments are situated one below the other and are separated by 1 or more plates positioned virtually horizontally.

8. Method according to claim 5, wherein the plates have 1 or more perforations and wherein the number and the size of the perforations are chosen such that the gas velocity through the holes which are designed for the passage of gas is between 0.2 m/s and 20 m/s.

9. Method according claim 5, wherein the plates have 1 or more perforations and wherein the size of the holes which are designed for the passage of gas is between 0.5 mm and 100 mm.

10. Method according to claim 5, wherein the plates have 1 or more perforations and wherein the total area of the perforations which are designed for the passage of gas is between 0.02% and 30% of the column cross-section.

11. Method according to claim 1, wherein the ammonia gas throughput and the column diameter are chosen such that the superficial gas velocity based on the total column cross-section is between 0.001 and 0.2 m/sec.

12. Method according to claim 1, wherein the melamine melt in the bubble column is cooled, at the same time, to a temperature between the incoming temperature and the crystallization temperature of the melamine melt.

13. Method according to claim 12, wherein the cooling is effected using ammonia gas having a temperature of between 150° C. and 350° C.

14. Method according to claim 1, wherein the amount of oxygen-containing compounds in the melamine end product is less than 0.7 wt %.

15. Method according to claim 1, wherein the amount of melam in the end product is less than 1.5 wt %.

16. Method according to claim 1, wherein the melamine content of the end product is greater than 98.5 wt %.

17. Method according to claim 7, wherein the plates have 1 or more perforations and wherein the number and the size of the perforations are chosen such that the gas velocity through the holes which are designed for the passage of gas is between 0.2 m/s and 20 m/s.

18. Method according to claim 7, wherein the plates have 1 or more perforations and wherein the size of the holes which are designed for the passage of gas is between 0.5 mm and 100 mm.

19. Method according to claim 7, wherein the plates have 1 or more perforations and wherein the total area of the perforations which are designed for the passage of gas is between 0.02% and 30% of the column cross-section.

* * * * *